(12) United States Patent
Chassot

(10) Patent No.: US 6,699,296 B2
(45) Date of Patent: Mar. 2, 2004

(54) P-DIAMINOBENZENE DERIVATIVES AND DYES CONTAINING SAID COMPOUNDS

(75) Inventor: Laurent Chassot, Praroman (CH)

(73) Assignee: Wella Aktiengesellschaft, Darmstadt (DE)

( * ) Notice: Subject to any disclaimer, the term of this patent is extended or adjusted under 35 U.S.C. 154(b) by 242 days.

(21) Appl. No.: 10/019,861

(22) PCT Filed: Feb. 20, 2001

(86) PCT No.: PCT/EP01/01860
§ 371 (c)(1),
(2), (4) Date: Nov. 9, 2001

(87) PCT Pub. No.: WO01/72686
PCT Pub. Date: Oct. 4, 2001

(65) Prior Publication Data
US 2003/0145764 A1 Aug. 7, 2003

(30) Foreign Application Priority Data
Mar. 24, 2000 (DE) .......................................... 100 14 855

(51) Int. Cl.$^7$ ................................................. A61K 7/13
(52) U.S. Cl. ...................... 8/405; 8/406; 8/410; 8/411; 8/412; 8/421; 564/305; 564/330
(58) Field of Search ............................ 8/405, 406, 410, 8/411, 412, 421; 564/305, 330

(56) References Cited

U.S. PATENT DOCUMENTS 4,842,612 A * 6/1989 Rose et al. .................... 8/411

FOREIGN PATENT DOCUMENTS

| DE | 198 22 047 A | 12/1999 |
| EP | 0 286 896 A | 10/1988 |

* cited by examiner

*Primary Examiner*—Yogendra N. Gupta
*Assistant Examiner*—Eisa Elhilo
(74) *Attorney, Agent, or Firm*—Michael J. Striker

(57) ABSTRACT p-Diaminobenzene derivatives of general formula (I) or physiologically tolerated water-soluble salts thereof

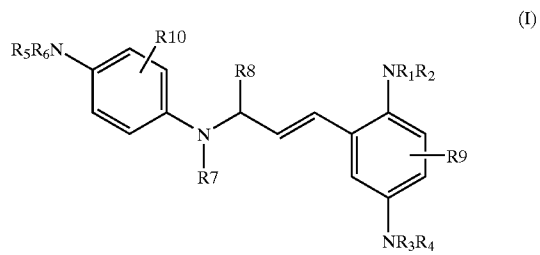

(I)

and their use as developers in oxidation colorants for keratin fibers.

11 Claims, No Drawings

P-DIAMINOBENZENE DERIVATIVES AND DYES CONTAINING SAID COMPOUNDS

The invention relates to novel p-diaminobenzene derivatives and to colorants for dyeing keratin fibers and containing these compounds.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 4-amino-3-methylphenol and 1,4-diaminobenzene, and suitable couplers are, for example, resorcinol, 4-chlororesorcinol, 1-naphthol, 3-aminophenol, 5-amino-2-methylphenol and derivatives of m-phenylenediamine. Moreover, Unexamined German Patent Application [DE-OS] 198 22 041 describes colorants containing as developers p-phenylenediamines substituted in the 2-position.

The oxidation dyes used for dyeing human hair must meet numerous requirements in addition to that of being able to produce colorations of the desired intensity. For example, these dyes must be harmless from a toxicological and dermatological standpoint, and the hair colorations must have good light fastness, resistance to permanent waving, acid fastness and rubbing fastness. In any case, however, such colorations must remain stable over a period of at least 4 to 6 weeks in the absence of exposure to light, rubbing and chemical agents. Moreover, by combination of appropriate developers and couplers, it must be possible to create a wide range of color shades.

Currently used colorants, however, do not meet all aspects of the aforesaid requirements.

Hence, there continues to exist a need for novel developers capable of meeting the aforesaid requirements to a very high degree.

Surprisingly, in this regard, we have now found that p-diaminobenzene derivative of general formula (I) meet the requirements placed on developers to a particularly high degree. For example, the use of these developers in combination with known couplers produces intense color shades that are unusually light-fast and wash-fast.

The object of the present invention are therefore p-diaminobenzene derivatives of general formula (I) or physiologically tolerated, water-soluble salts thereof

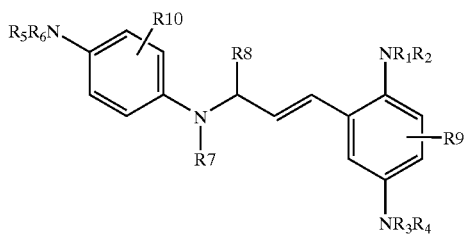

(I)

wherein R1, R2, R3, R4, R5, R6 and R7 independently of each other denote hydrogen, a $C_1$–$C_6$-alkyl group, a $C_1$–$C_4$-hydroxyalkyl group, a $C_2$–$C_4$-dihydroxyalkyl group or a $C_1$–$C_4$-alkoxy-($C_1$–$C_4$)-alkyl group, or R1 and R2 or R3 and R4 or R5 and R6 form a four-membered to eight-membered aliphatic ring, and at least two of the R1 to R7 groups denote hydrogen;

R8 stands for hydrogen or a $C_1$–$C_4$-alkyl group; and

R9, R10 independently of each other denote hydrogen, a hydroxyl group, a halogen atom, a $C_1$–$C_4$-alkyl group, a $C_1$–$C_4$-hydroxyalkyl group, a $C_1$–$C_4$-aminoalkyl, group, an amino group, a $C_1$–$C_2$-alkylamino group or a $C_1$–$C_4$-alkoxy group.

Suitable compounds of formula (I) are, for example:
4-[3-(2,5-diaminophenyl)allylamino]aniline; 4-[3-(2,5-diaminophenyl)-2-(2-hydroxyethyl)-aniline; 4-[3-(2,5-diaminophenyl)allylamino]-5-(2-hydroxyethyl)aniline; 4-[3-(2,5-diaminophenyl)allylamino]-2-chloroaniline; 4-[3-(2,5-diaminophenyl)allylamino]-2-methylaniline; 4-[3-(2,5-diaminophenyl)allylamino]-3-(2-hydroxyethyl)aniline; 4-[3-(2,5-diaminophenyl)allylamino]-3-chloroaniline; 4-[3-(2,5-diaminophenyl)allylamino]-3-methylaniline; 4-{3-[2,5-diamino-3-(2-hydroxyethyl)phenyl]allylamino}-aniline; 4-[3-(2,5-diamino-3-chlorophenyl)allylamino]aniline; 4-[3-(2,5-diamino-3-methylphenyl)allyl]-amino]aniline; 4-[3-(2,5-diamino-6-methylphenyl)allylamino]aniline; 4-{3-[2,5-diamino-4-(2-hydroxyethyl)phenyl]allylamino}aniline; 4-[3-(2,5-diamino-4-chlorophenyl)allylamino]aniline; 4-[3-(2,5-diamino-4-methylphenyl)allylamino]aniline; 4-[3-($N^2$,$N^2$-bis-methyl-2,5-diaminophenyl)allylamino]-2-aniline; 4-{3-[$N^2$,$N^2$-bis-(2-hydroxyethyl)-2,5-diaminophenyl]allylamino}-2-aniline; 4-[3-($N^5$,$N^5$-bis-methyl-2,5-diaminophenyl)allylamino]-2-aniline; 4-{3-[$N^5$,$N^5$-bis-(2-hydroxyethyl)-2,5-diaminophenyl]-allylamino}-2-aniline; 4-[3-(2,5-diaminophenyl)allylamino]-2-N,N'-bis-methylaniline; 4-[3-(2,5-diaminophenyl)allylamino]-2-N,N'-bis-(2-hydroxyethyl)aniline or a physiologically tolerated salt thereof.

Preferred are compounds of formula (I) wherein (i) at least one of groups R8 to R10 denotes hydrogen, and/or (ii) R1 and R2 or R3 and R4 or R5 and R6 or all R1 to R4 or R1 to R7 groups denote hydrogen. Also preferred are compounds of formula (I) wherein R8 denotes hydrogen and R5 and R6 independently of each other denote hydrogen, a $C_1$–$C_4$-alkyl group, a $C_1$–$C_4$-hydroxyalkyl group or a $C_2$–$C_4$-dihydroxyalkyl group.

Particularly preferred p-diaminobenzene derivatives of formula (I) are 4-[3-(2,5-diaminophenyl)-allylamino]aniline; 4-[3-(2,5-diaminophenyl)allylamino]-2-(2-hydroxyethyl)aniline; 4-[3-(2,5-diaminophenyl)allylamino]-2-methylaniline; 4-[3-(2,5-diaminophenyl)allylamino]-3-methylaniline; 4-[3-(2,5-diaminophenyl)allylamino]-3-(2-hydroxyethyl)aniline; 4-[3-(2,5-diaminophenyl)allylamino]-2-N,N'-bis-methylaniline; 4-[3-(2,5-diaminophenyl)allylamino]-2-N,N'-bis-(2-hydroxyethyl)aniline or physiologically tolerated salts thereof.

The compounds of formula (I) can be used either as free bases or in the form of their physiologically tolerated salts of inorganic or organic acids, for example hydrochloric acid, sulfuric acid, phosphoric acid, acetic acid, propionic acid, lactic acid or citric acid.

The p-diaminobenzene derivatives of formula (I) can be prepared by known methods of synthesis. For example, the synthesis of the compounds of the invention can be carried out as follows:

By reductive amination of a substituted benzene of formula (II)

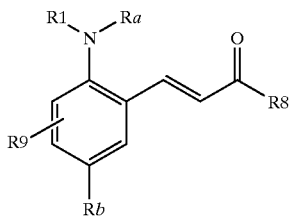

wherein Ra denotes a suitable protective group described, for example, in Organic Synthesis, Chapter 7 "Protection for the Amino Group", page 309 ff., Wiley Interscience, 1991; Rb has the meaning of NR1Ra or NR1R2, with an amine of formula (III)

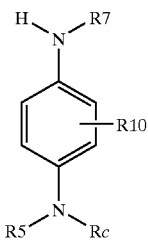

wherein Rc has the meaning of Ra or R6, R5, R6, R7, R8, R9 and R10 having the same meaning as in formula (I), followed by elimination of the protective group.

The p-diaminobenzene derivatives of formula (I) of the invention are readily water-soluble and give colorations of high color intensity and excellent color fastness, particularly in terms of light fastness, wash fastness and rubbing fastness. The compounds of formula (I) also have excellent storage stability, particularly as constituents of the colorants described in the following.

Hence, another object of the present invention are compositions for oxidative dyeing of keratin fibers, for example hair, furs, feathers or wool, particularly human hair, based on a developer-coupler combination, said compositions containing as the developer at least one p-diaminobenzene derivative of formula (I).

The p-diaminobenzene derivatives of formula (I) are contained in the colorants of the invention in a total amount of about 0.005 to 20 wt. %, an amount from about 0.01 to 5.0 wt. % and particularly from 0.1 to 5 wt. % being preferred.

Preferred couplers are 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methyl-benzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]aniline, 4-amino-2-di-[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di-(2,4-diaminophenoxy)propane, di-(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Although the advantageous properties of the p-diaminobenzene derivatives of formula (I) described here suggest that said derivatives should be used as the only developers, it is, of course, also possible to use the p-diaminobenzene derivatives of formula (I) together with known developers such as, for example, 1,4-diaminobenzene, 2,5-diaminotoluene, 2,5-diaminophenylethyl alcohol, 4-aminophenol and the derivatives thereof, for example 4-amino-3-methylphenol, 4,5-diaminopyrazole derivatives, for example 4,5-diamino-1-(2-hydroxyethyl)pyrazole, or tetraaminopyrimidines.

The couplers and developers can be contained in the colorants of the invention either alone or in admixture with each other, the total amount of couplers and developers in the colorants of the invention (based on the total amount of colorant) being in all cases from 0.005 to 20 wt. %, preferably from about 0.01 to 5.0 wt. % and particularly from 0.1 to 2.5 wt. %.

The total amount of developer-coupler combination contained in the colorants described here is preferably from about 0.01 to 20 wt. %, an amount from about 0.02 to 10 wt. % and particularly from 0.2 to 6.0 wt. % being particularly preferred. In general, the developers and couplers are used in approximately equimolar amounts. It is not disadvantageous in this respect, however, if the developers are present in a certain excess or deficiency (for example, in a coupler-to-developer ratio of 1:2 to 1:0.5).

Moreover, the colorants of the invention can additionally contain other dye components, for example 6-amino-2-methylphenol and 2-amino-5-methylphenol, as well as other common direct dyes, for example triphenylmethane dyes such as 4-[(4'-aminophenyl)-(4'-imino-2",5"-cyclohexadien-1"-ylidene)methyl]-2-methylaminobenzene monohydrochloride (C.I.[1] 42 510) and 4-[(4'-amino-3'-methylphenyl)-(4"-imino-3"-methyl-2",5"-cyclohexadien-1"-ylidene)methyl]-2-methylaminobenzene monohydrochloride (C.I.

42 520), aromatic nitro dyes such as 4-(2'-hydroxyethyl)aminonitrotoluene, 2-amino-4,6-dinitrophenol, 2-amino-5-(2'-hydroxyethyl)aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino]-4-nitrobenzene, azo dyes such as sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone.

[1] C.I.=Color Index-Translator

The colorants of the invention can contain these dye components in an amount from about 0.1 to 4.0 wt. %.

Naturally, the couplers and developers and the other dye components, as long as they are bases, can also be used in the form of physiologically tolerated salts of organic or inorganic acids, for example hydrochloric acid or sulfuric acid or—providing that they contain aromatic OH groups—in the form of salts of bases, for example as alkali metal phenoxides.

Moreover, if the colorants are to be used for coloring hair, they can contain other common cosmetic additives, for example antioxidants such as ascorbic acid, thioglycolic acid or sodium sulfite, as well as perfume oils, complexing agents, wetting agents, emulsifiers, thickeners and hair-care agents. The colorant of the invention can be formulated as a solution, particularly as an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5.0 wt. %.

Depending on the composition, the colorants of the invention can be weakly acidic, neutral or alkaline. Preferably, the colorants of the invention have a pH of 5 to 11.5, a pH of about 6.5 to 10.5 being particularly preferred. Adjustment to a basic pH is preferably done with ammonia, but it can also be done with an organic amine, for example monoethanolamine and triethanolamine, or even with an inorganic base such as sodium hydroxide or potassium hydroxide. Suitable for adjustment to an acidic pH are inorganic or organic acids, for example phosphoric acid, acetic acid, citric acid or tartaric acid.

For oxidative dyeing of hair, the afore-described colorants are mixed with an oxidant just before use, and the resulting mixture is applied to hair in an amount sufficient for the hair-dyeing treatment, in general about 60 to 200 grams, depending on the hair fullness.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a p-diaminobenzene derivative of formula (I) as developer give hair colorations of excellent color fastness, particularly in terms of light fastness, wash fastness and rubbing fastness. As far as the dyeing properties are concerned, the hair colorants of the invention provide a wide range of different color shades from blond to brown, purple, violet and even blue and black, depending on the type and composition of the dye components. Such color shades are characterized by unusual color intensity. The very good coloring properties of the hair colorant of the present invention also manifest themselves in that these colorants make it possible to dye graying hair, chemically not previously damaged, without any problems and with good covering power.

The following examples will explain the object of the invention without limiting its scope.

EXAMPLES

I. Preparation Examples

Example 1

Synthesis of 4-[3-(2,5-Diaminophenyl)allylamino]aniline Derivatives of Formula (I) (General Method of Synthesis)
A. Synthesis of 2,5-Bis-tert.butyloxycarbonylaminobrombenzene 15.65 g (0.07 mole) of bromo-p-phenylenediamine hydrochloride and 32.7 g (0.15 mole) of di-tert.butyl dicarbonate were dissolved in a mixture of 250 mL of 2 N sodium hydroxide and 250 mL of trifluorotoluene, and the solution was heated to 45° C. The reaction mixture was then allowed to agitate for 3 days. An additional total of 30 g (0.14 mole) of di-tert.butyl dicarbonate was added stepwise. The organic layer was separated, and the aqueous phase was extracted twice more with 100-mL portions of dichloromethane. The combined extracts were evaporated, and the residue was taken up in 200 mL of hexane. The precipitate formed was filtered off and washed with 50 mL of hexane.

This gave 18.6 g (82% of the theoretical) of 2,5-tert.butyloxycarbonylaminobromobenzene with a melting point of 130° C.

B. Synthesis of tert-Butyl N-(4-tert.butyloxycarbonylamino-2-formylphenyl)carbamate 3.3 g (0.01 mole) of 2,5-tert.butyloxycarbonylaminobromobenzene from step A was dissolved in 100 mL of anhydrous tetrahydrofuran under argon. To this solution was then added stepwise 17 mL of a 1.6 molar solution of methyllithium in ether (0.03 mole). The reaction mixture was cooled to −20° C., and to it was added stepwise 7 mL of a 1.5 molar tert.butyllithium solution (0.01 mole). At the end of the addition, the solution was allowed to agitate at the indicated temperature for an addi-tional 30 minutes. Then, 1.2 g of dimethylformamide (0.02 mole) was added, and the reaction mixture was allowed to agitate at −20° C. for an hour. The reaction mixture was slowly brought to room temperature and then subjected to hydrolysis with water. It was then poured onto diethyl ether. The aqueous phase was extracted with diethyl ether, and the organic phase was dried over magnesium sulfate. The solvent was distilled off in a rotary evaporator, and the residue was purified on silica gel with petroleum ether/ethyl acetate (9:1).

C. Synthesis of tert.Butyl N-[4-tert.butoxycarbonylamino-3-(3-oxopropenyl)phenyl]carbamate 9.5 g (0.03 mole) of tert.butyl N-tert.butyloxycarbonylamino-2-formylphenyl)carbamate from step B was dissolved in 100 mL of tetrahydrofuran, and to this solution was added 10.2 g (0.035 mole) of formylmethyltriphenylphosphorane. The reaction mixture was allowed to agitate at 60° C. for 18 hours. The reaction mixture was then poured into water and extracted with ethyl acetate. The organic phase was washed with a saturated aqueous NaCl solution, dried over sodium sulfate, filtered and then concentrated. Flash chromatography of the crude product on silica gel with hexane/EtOAc gave 4.84 g (47% of the theoretical).

$^1$H-NMR (300 MHz, CDCl$_3$)

9.68 (d; J=7.6; 1H); 7.66 (d; J=2.2, 1H); 7.57 (d; J=15.9; 1H); 7.43 (d; J=8.6; 1H); 7.28 (dd; J$^1$=2.4; J$^2$=8.7; 1H); 6.75 (s; 1H); 6.61 (dd; J$^1$=7.6; J$^2$=15.9; 1H); 6.51 (s; 1H); 1.51 (s; 18H).

D. Synthesis of 4-[3-(2,5-Diaminophenyl)allylamino]anilines 0.036 g (0.0001 mole) of tert.butyl N-(4-tert.butoxycarbonylamino-3-(3-oxopropenyl)phenyl]carbamate from step C and 0.00015 mole of the corresponding amine were dissolved in 1,2-dichloroethane. Then, 0.1 mL of an acetic acid solution (1 M in 1,2-dichloroethane) and 0.06 g of NaBH(OAc)$_3$ (0.0003 mole) were added, and the reaction mixture was allowed to agitate 5 to 15 hours at room temperature. At the end of the reaction, the reaction mixture was poured into 10 mL of ethyl acetate and the organic phase was extracted with a saturated sodium hydrogen carbonate solution and then dried with magnesium sulfate. The solvent was distilled off in a rotary evaporator, and the residue was purified on silica gel with petroleum ether/ethyl acetate (9:1). The product obtained in this manner was heated to 50° C. in 4 mL of ethanol. To form the hydrochloride, 1.5 mL of 2.9 molar ethanolic hydrochloric acid solution was added dropwise. The precipitate was filtered off, washed twice with 1 mL of ethanol and then dried.

1a. 4-[3-(2,5-Diaminophenyl)allylamino]aniline Hydrochloride

Amine used: 4-tert.butyloxycarbonylaminoaniline
    Yield: 0.025 g (95% of the theoretical)
    Mass spectrum: M$^+$ 254 (20)

1b. 4-[3-(2,5-Diaminophenyl)allylamino]-3-methylaniline Hydrochloride and 4-[3-(2,5-Diaminophenyl)allylamino]-2-methylaniline Hydrochloride Amine used: 4-tert.butyloxycarbonylamino-3-methylaniline and 4-tert.butyloxycarbonylamino-2-methylaniline, respectively
    Yield: 0.025 g (93% of the theoretical)
    Mass spectrum: M$^+$ 268 (20)

1c. 2-{5-Amino-2-[3-(2,5-diaminophenyl)allylamino]phenyl}ethanol Hydrochloride and 2-{2-Amino-5-[3-(2,5-diaminophenyl)allylamino]phenyl}ethanol Hydrochloride Amine used: 4-tert.butyloxycarbonylamino-3-(2-hydroxyethyl)aniline and 4-tert.butyloxycarbonylamino-2-(2-hydroxyethyl)aniline, respectively
    Yield: 0.025 g (56% of the theoretical)
    Mass spectrum: MH$^+$ 299 (100)

Examples 2 to 4

Hair Colorants

Hair colorant solutions having the following composition were prepared:

| | |
|---|---|
| 1.25 mmoles | of a developer of formula (I) according to Table 1 |
| 1.25 mmoles | of a coupler according to Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Immediately before use, 50 g of the foregoing coloring solution was mixed with 50 g of a 6% aqueous solution of hydrogen peroxide. The mixture was then applied to bleached hair. After an exposure time of 30 min at 40° C., the hair was rinsed with water, washed with a commercial shampoo and dried. The resulting colorations are presented in Table 1.

TABLE 1

| | | Coupler | | | |
|---|---|---|---|---|---|
| Example | Developer of formula (I) | I. 1,3-Dihydroxybenzene | II. 1,3-Diamino-4-(2-hydroxyethoxy)-benzene sulfate | III. 5-Amino-2-methylphenol | IV. 1-Naphtol |
| 2. | as per Example 1a | dark-blond | blue | purple | violet |
| 3. | as per Example 1b | medium-blond | blue | purple | gray-violet |
| 4. | as per Example 1c | bright, light-blond | blue | purple | violet |

Examples 5 to 14

Hair Colorants

Hair colorant solutions having the following composition were prepared:

| | |
|---|---|
| X g | of 4-[3-(2,5-diaminophenyl)allylamino]aniline hydrochloride [developer E1 of formula (I)] |
| U g | of develpoer E2 to E9 according to Table 2 |
| Y g | of coupler K11 to K36 according to Table 4 |
| Z g | of direct dye D1 to D3 according to Table 3 |
| 10.000 g | of potassium oleate (8% aqueous solution) |
| 10.000 g | of ammonia (22% aqueous solution) |
| 10.000 g | of ethanol |
| 0.300 g | of ascorbic acid |
| to 100.000 g | water |

Immediately before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. The coloring results are presented in Table 5.

Examples 15 to 20

Hair Colorants

Dye carriers in cream form and having the following composition were prepared:

| | |
|---|---|
| X g | of 4-[3-(2,5-diaminophenyl)allylamino]aniline hydrochloride [developer E1 of formula (I)] |
| Y g | of coupler K11 to K36 according to Table 4 |
| Z g | of direct dye D2 according to Table 3 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100 g | water |

Immediately before use, 30 g of the foregoing coloring cream was mixed with 30 g of a 6% aqueous solution of hydrogen peroxide. The mixture was then applied to bleached hair. After an exposure time of 30 min, the hair was rinsed with water, washed with a commercial shampoo and dried. The coloring results are presented in Table 6.

TABLE 2

Developers

| | |
|---|---|
| E2 | 1,4-Diaminobenzene |
| E3 | 2,5-Diaminophenylethanol sulfate |
| E4 | 3-Methyl-4-aminophenol |
| E5 | 4-Amino-2-aminomethylphenol dihydrochloride |
| E6 | 4-Aminophenol |
| E7 | N,N-Bis-(2'-hydroxyethyl)-p-phenylenediamine sulfate |
| E8 | 4,5-Diamino-1-(2'-hydroxyethyl)pyrazole sulfate |
| E9 | 2,5-Diaminotoluene sulfate |

TABLE 3

Direct Dyes

| | |
|---|---|
| D1 | 2,6-Diamino-3-[(pyridin-3-yl)azo]pyridine |
| D2 | 6-Chloro-2-ethylamino-4-nitrophenol |
| D3 | 2-Amino-6-chloro-4-nitrophenol |

TABLE 4

Couplers

| | |
|---|---|
| K11 | 1,3-Diaminobenzene |
| K12 | 2-Amino-4-(2'-hydroxyethyl)aminoanisole sulfate |
| K13 | 1,3-Diamino-4-(2'-hydroxyethoxy)benzene sulfate |
| K14 | 2,4-Diamino-5-fluorotoluene sulfate |
| K15 | 3-Amino-2-methylamino-6-methoxypyridine |
| K16 | 3,5-Diamino-2,6-dimethoxypyridine dihydrochloride |
| K17 | 2,4-Diamino-5-ethoxytoluene sulfate |
| K18 | N-(3-Dimethylamino)phenylurea |
| K19 | 1,3-Bis-(2,4-diaminophenoxy)propane tetrahydrochloride |
| K21 | 3-Aminophenol |
| K22 | 5-Amino-2-methylphenol |
| K23 | 3-Amino-2-chloro-6-methylphenol |
| K24 | 5-Amino-4-fluoro-2-methylphenol sulfate |
| K25 | 1-Naphthol |
| K26 | 1-Acetoxy-2-methylnaphthalene |
| K31 | 1,3-Dihydroxybenzene |
| K32 | 2-Methyl-1,3-dihydroxybenzene |
| K33 | 1-Chloro-2,4-dihydroxybenzene |
| K34 | 4-(2'-Hydroxyethyl)amino-1,2-methylenedioxybenzene hydrochloride |
| K35 | 3,4-Methylenedioxyphenol |
| K36 | 2-Amino-5-methylphenol |

TABLE 5

Hair Colorants

| Dye | (Quantity of dye in grams) | | | |
|---|---|---|---|---|
| Example No. | 5 | 6 | 7 | 8 |
| E1 | 0.35 | 0.3 | 0.3 | 0.30 |
| E4 | 0.30 | | | |
| E5 | | 0.30 | | |
| E6 | | | 0.30 | |
| E8 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Resulting color | red-br. | red-br. | red-br. | red-br. |

| Example No. | 9 | 10 | 11 | 12 | 13 | 14 |
|---|---|---|---|---|---|---|
| E1 | 0.50 | 0.4 | 0.4 | 0.16 | 0.15 | 0.15 |
| E2 | | | | 0.15 | | |
| E3 | | | | | 0.15 | |
| E9 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Resulting color | blond | blond | blond | blond | blond | blond | red-br. = red-brown

TABLE 6

Hair Colorants

| Dye | (Quantity of dye in grams) | | | | | |
|---|---|---|---|---|---|---|
| Example No. | 15 | 16 | 17 | 18 | 19 | 20 |
| E1 | 2.50 | 2.50 | 2.50 | 0.90 | 0.90 | 0.90 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Resulting color | black | black | black | brown | brown | brown |

Unless otherwise indicated, all percentages given in the present patent application are by weight.

What is claimed is:

1. p-Diaminobenzene derivatives of general formula (I) or physiologically tolerated, water-soluble salts thereof

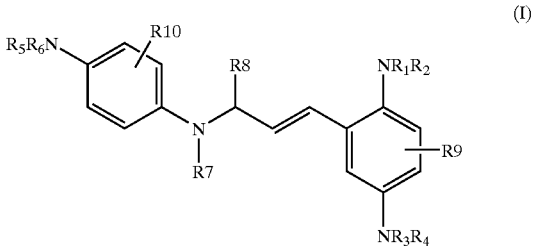

(I)

wherein

R1, R2, R3, R4, R5, R6 and R7 independently of each other denote hydrogen, a $C_1$–$C_6$-alkyl group, a $C_1$–$C_4$-hydroxyalkyl group, a $C_2$–$C_4$-dihydroxyalkyl group or a $C_1$–$C_4$-alkoxy-($C_1$–$C_4$)-alkyl group, or R1 and R2 or R3 and R4 or R5 and R6 form a four-membered to eight-membered aliphatic ring, and wherein at least two of the R1 to R7 groups denote hydrogen;

R8 stands for hydrogen or a $C_1$–$C_4$-alkyl group; and

R9, R10 independently of each other denote hydrogen, a hydroxyl group, a halogen atom, a $C_1$–$C_4$-alkyl group, a $C_1$–$C_4$-hydroxyalkyl group, a $C_1$–$C_4$-aminoalkyl group, an amino group, a $C_1$–$C_2$-alkylamino group or a $C_1$–$C_4$-alkoxy group.

2. p-Diaminobenzene derivative according to claim 1, characterized in that in formula (I) (i) at least one of groups R8 to R10 denotes hydrogen and/or (ii) R1 and R2 or R3 and R4 or R5 and R6 or all groups from R1 to R4 or from R1 to R7 denote hydrogen.

3. p-Diaminobenzene derivative according to claim 1, characterized in that in formula (I) R8 denotes hydrogen and R5 and R6 independently of each other denote hydrogen, a $C_1$–$C_4$-alkyl group, a $C_1$–$C_4$-hydroxyalkyl group or a $C_2$–$C_4$-dihydroxyalkyl group.

4. p-Diaminobenzene derivative according to claim 1, characterized in that it is selected from the group consisting of 4-[3-(2,5-diaminophenyl)allylamino]aniline; 4-[3-(2,5-diaminophenyl)allylamino]-2-(2-hydroxyethyl)aniline; 4-[3-(2,5-diaminophenyl)allylamino]-5-(2-hydroxyethyl)aniline; 4-[3-(2,5-diaminophenyl)allylamino]-2-chloroaniline; 4-[3-(2,5-diaminophenyl)-allylamino]-2-methylaniline; 4-[3-(2,5-diaminophenyl)allylamino]-3-(2-hydroxyethyl)aniline; 4-[3-(2,5-diaminophenyl)allylamino]-3-chloroaniline; 4-[3-(2,5-diaminophenyl)allylamino]-3-methylaniline; 4-{3-[2,5-diamino-3-(2-hydroxyethyl)phenyl]allylamino}aniline; 4-[3-(2,5-diamino-3-chlorophenyl)allylamino]aniline; 4-[3-(2,5-diamino-3-methylphenyl)allylamino]aniline; 4-[3-(2,5-diamino-6-methylphenyl)allylamino]aniline; 4-{3-[2,5-diamino-4-(2-hydroxyethyl)phenyl]allylamino}aniline; 4-[3-(2,5-diamino-4-chlorophenyl)allylamino]aniline; 4-[3-(2,5-diamino-4-methylphenyl)allylamino]aniline; 4-[3-($N^2$,$N^2$-bis-methyl-2,5-diaminophenyl)allylamino]-2-aniline; 4-{3-[$N^2$,$N^2$-bis-(2-hydroxyethyl)-2,5-diaminophenyl]allylamino}-2-aniline; 4-[3-($N^5$,$N^5$-bis-methyl-2,5-diaminophenyl)allylamino]-2-aniline; 4-{3-[$N^5$, $N^5$-bis-(2-hydroxyethyl)-2,5-diaminophenyl]allylamino}-2-aniline; 4-[3-(2,5-diaminophenyl)-allylamino]-2-N,N'-bis-methylaniline; 4-[3-(2,5-diaminophenyl)allylamino]-2-N,N'-bis-(2-hydroxyethyl)-aniline or a physiologically tolerated salt thereof.

5. Colorant for oxidative dyeing of keratin fibers based on a developer-coupler combination, characterized in that it contains as the developer at least one p-diaminobenzene derivative of formula (I) according to claim 1.

6. Colorant according to claim 5, characterized in that it contains the diaminobenzene derivative of formula (I) in an amount from 0.005 to 20 wt. %.

7. Colorant according to claim 5 characterized in that the coupler is selected from the group consisting of 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methyl-benzene, 2,4-diamino-1-(2-hydroxyethoxy)-5-methylbenzene, 2,4-di[(2-hydroxyethyl) amino]-1,5-dimethoxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]aniline, 4-amino-2-di-[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di-(2,4-diaminophenoxy)propane, di-(2,4-diaminophenoxy) methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl) amino]-2-methylphenol, 3-[(2-hydroxyethyl)amino]phenol, 3[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

8. Colorant according to claim 5, characterized in that besides the p-diaminobenzene derivative of formula (I) it contains at least one additional developer selected from the group consisting of 1,4-diaminobenzene, 2,5-diaminotoluene, 2,5-diaminophenylethyl alcohol, 4-aminophenol and derivatives thereof, 4,5-diaminopyrazole derivatives and tetraaminopyrimidines.

9. Colorant according to claim 5, characterized in that it contains the developers and couplers in a total amount of 0.005 to 20 wt. %, based on the total amount of the colorant.

10. Colorant according to claim 5, characterized in that it contains additionally at least one direct dye.

11. Colorant according to claim 5, characterized in that it is a hair colorant.

* * * * *